United States Patent [19]

Chin

[11] Patent Number: 5,797,946
[45] Date of Patent: Aug. 25, 1998

[54] METHOD FOR ARTERIAL HARVEST AND ANASTOMOSIS FOR CORONARY BYPASS GRAFTING

[75] Inventor: Albert K. Chin, Palo Alto, Calif.

[73] Assignee: Origin Medsystems, Inc., Menlo Park, Calif.

[21] Appl. No.: 616,206

[22] Filed: Mar. 15, 1996

Related U.S. Application Data

[63] Continuation-in-part of Ser. No. 593,533, Jan. 24, 1996, abandoned, which is a continuation-in-part of Ser. No. 502,494, Jul. 13, 1995.

[51] Int. Cl.$^6$ ................................................ A61B 17/00
[52] U.S. Cl. .................... 606/190; 606/192; 606/159; 128/898
[58] Field of Search .............................. 606/190, 192, 606/159; 128/898

[56] References Cited

U.S. PATENT DOCUMENTS

| | | | |
|---|---|---|---|
| 5,373,840 | 12/1994 | Knighton | 128/4 |
| 5,591,183 | 1/1997 | Chin | 606/159 |
| 5,593,418 | 1/1997 | Mollenauer | 606/194 |
| 5,601,589 | 2/1997 | Fogarty et al. | 606/207 |

*Primary Examiner*—Michael Buiz
*Assistant Examiner*—Daphna Shai
*Attorney, Agent, or Firm*—Fenwick & West LLP

[57] ABSTRACT

A method of harvesting arterial conduits for coronary bypass grafting includes isolating the internal mammary artery and the superior and inferior epigastric arteries through a subcostal incision using a tapered tip balloon dissection cannula. A free end of the isolated artery may be anastomosed to the coronary artery, and a free graft harvested from the inferior epigastric artery may be anastomosed to the subclavian artery for an additional coronary bypass conduit.

14 Claims, 6 Drawing Sheets

5,797,946

METHOD FOR ARTERIAL HARVEST AND ANASTOMOSIS FOR CORONARY BYPASS GRAFTING

RELATED APPLICATIONS

This application is a continuation-in-part application of application Ser. No. 08/593,533, entitled "Tissue Dissection Cannula with Dissection Probe and Method", filed on Jan. 24, 1996 by Albert K. Chin and now abandoned, which is a continuation-in-part application of pending application Ser. No. 08/502,494, entitled "Tissue Separation Cannula and Method", filed on Jul. 13, 1995 by Albert K. Chin and is still pending.

FIELD OF THE INVENTION

This invention relates to harvesting blood vessels for coronary bypass grafting, and more particularly to techniques for facilitating harvesting the mammary artery for anastomosis to the coronary artery using minimally invasive procedures.

BACKGROUND OF THE INVENTION

A minimally invasive technique for coronary artery bypass grafting, using a Chamberlain approach for cardiac access, is performed by a parasternal approach, making a skin incision over the third costal cartilage and resecting the cartilage to provide access to the heart and the left anterior descending artery of the heart. Over the past two years, several cardiac surgeons have used this approach to perform coronary artery bypass surgery. The internal mammary artery has been used as the donor vessel, and a short length (4 or 5 cm) of the internal mammary artery is dissected from the interior of the chest wall via the parasternal incision. Side branches present in the length of the dissected internal mammary artery are occluded using vessel clips or suture ties, and transected to provide a free length of the internal mammary artery which may be sewn into the coronary artery at the site of the bypass. The distal anastomosis to the coronary artery may be performed on a beating heart, without the institution of cardiopulmonary bypass. Medication may be administered to slow the heartbeat (pharmacologic bradycardia) and render it easier to sew the graft onto the coronary artery.

This approach is hampered by the limited length of the internal mammary artery which can be harvested via the small parasternal thoracotomy incision, thus making it difficult to reach some desired coronary artery bypass sites. It is also difficult to gain access to proximal branches arising from the internal mammary artery. These branches are usually ligated to ensure that blood flow through the graft supplies the coronary artery, rather than being shunted off to other regions via various open branches. At present, use of the right and the left internal mammary arteries may supply two coronary bypass grafts.

SUMMARY OF THE INVENTION

In accordance with the present invention, sufficient donor arterial graft material is harvested to provide four coronary bypass grafts. Arterial graft conduits are preferable to vein grafts, due to their improved long term patency rates. As described in the Related Applications cited above, a tapered tip balloon cannula may be introduced from a subxiphoid incision, placed in contact with the isolated superior epigastric artery, and passed proximally to harvest the internal mammary artery. The cannula may be advanced to the origin of the internal mammary artery at the subclavian artery. The cannula may be advanced in the opposite direction also to isolate and harvest the inferior epigastric artery, (which is a continuation of the superior epigastric artery). The harvested inferior epigastric artery may be transected and used as a free graph to bypass a diseased coronary artery. The proximal anastomosis of the free graph may be performed on the subclavian artery by making an incision just above or just below the clavicle near its midpoint, to expose the subclavian artery. Following completion of the proximal anastomosis, a subcutaneous tunnel may be formed from the clavicle to the third intercostal space, which is the access incision used for coronary bypass grafting. The free graft is pulled down through the subcutaneous tunnel and the distal anastomosis performed to the desired coronary artery. The harvested internal mammary artery is introduced into the mediastinum via an incision in the parietal pleura, which covers the internal mammary artery posteriorly, and the pericarium, and is anastomosed to bypass a second coronary artery.

The above described technique permits at least four coronary bypass grafts to be performed including bilateral internal mammary to coronary artery grafts, and two subclavian to coronary artery grafts using the inferior epigastric arteries as free grafts.

DETAILED DESCRIPTION OF THE INVENTION

Figure 1:
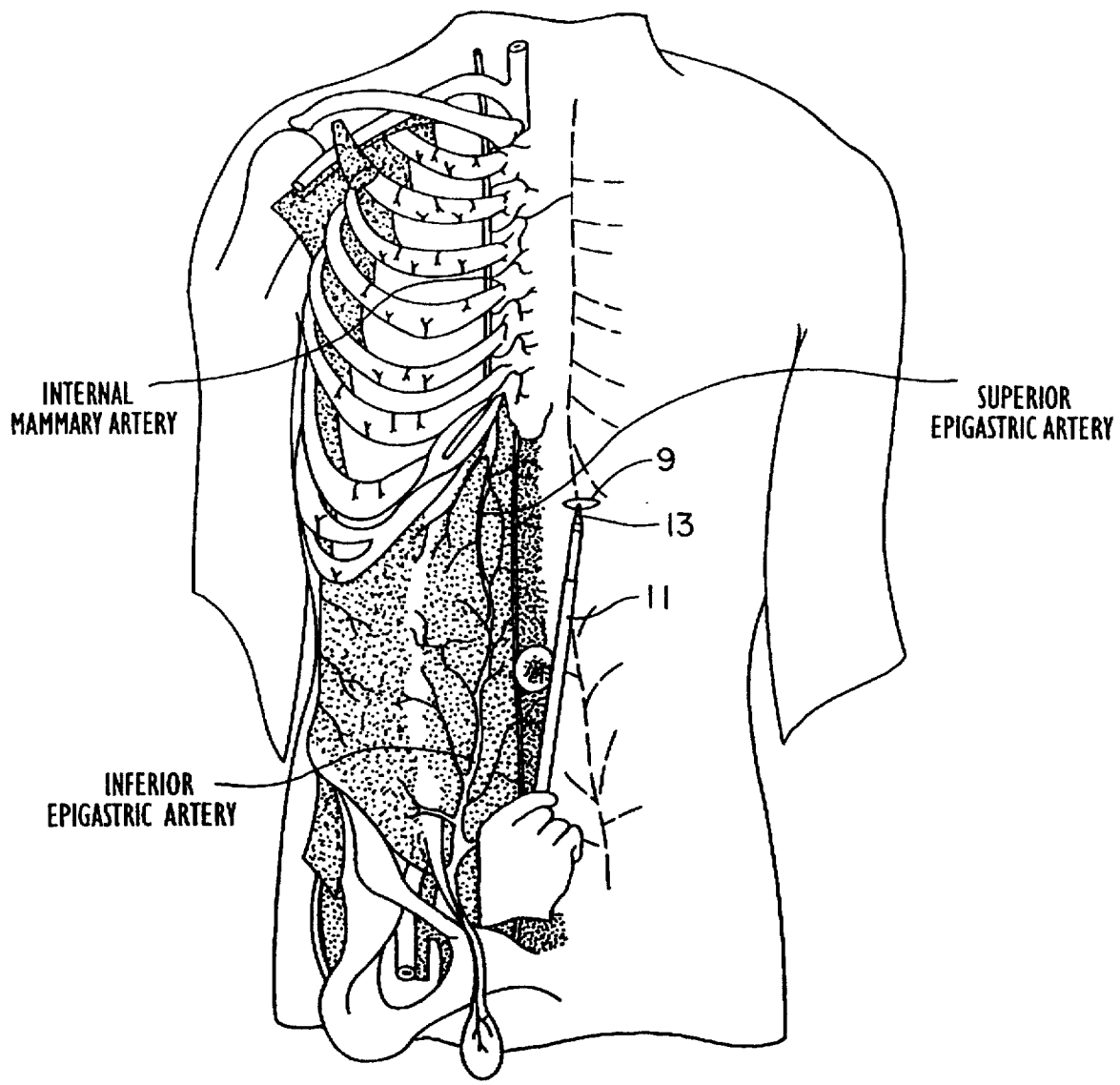
FIG. 1 is a partial anatomical drawing illustrating the course of the internal mammary artery and the orientation of a tapered tip balloon dissection catheter in the superior direction from a sub-costal incision.

Referring now to the partial anatomical illustration of FIG. 1, there is shown the right side of the human torso showing the course of the internal mammary artery, or anterior thoracic artery, oriented down the chest wall behind the rib cage. This artery continues as the superior epigastric artery within the rectus muscle, and continues as the inferior epigastric artery at the distal extent. Similarly, in the left side of the torso, the internal mammary artery is oriented down the chest wall behind the rib cage, and FIG. 1 illustrates a subcostal incision 9 used to expose the superior epigastric artery. A tapered transparent tip, balloon dissection cannula 11, as illustrated and described in the Related Applications cited above, is inserted into the incision superiorly to dissect a working cavity within the tissue planes along the course of the internal mammary artery in the manner as described in the aforecited Related Applications. Briefly, the tapered tip 13 of the cannula 11 is advanced along the internal mammary artery while visualizing the course of the artery through the transparent tapered tip. A peripheral balloon adjacent the tapered tip is selectively inflated and deflated, and the tip advanced, to dissect tissue and form an extended working cavity adjacent the superior epigastric artery and internal mammary artery substantially to the juncture with the subclavian artery.

Figure 2:
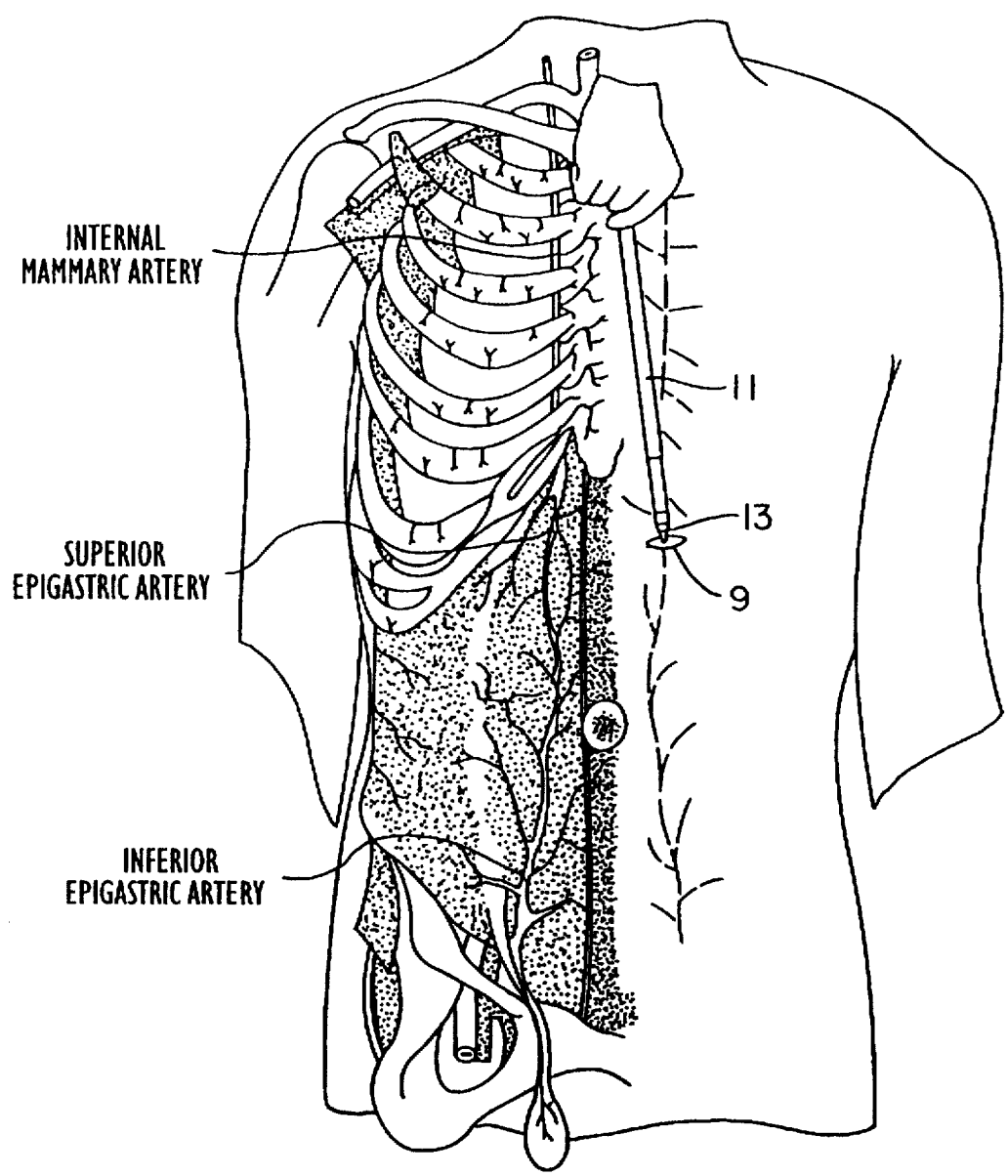
FIG. 2 is the partial anatomical drawing of FIG. 1 illustrating the orientation of a tapered tip balloon dissection catheter in the inferior direction from a subcostal incision.

Referring now to the partial anatomical drawing of FIG. 2, there is shown the tapered tip balloon cannula 11 in an inferior orientation from the subcostal incision 9. In this orientation, the tapered tip 13 of the cannula may be advanced along the course of the superior epigastric and inferior epigastric arteries, and the peripheral balloon selectively inflated and deflated with the tapered tip being selectively advanced, all as fully described in the aforecited Related Applications, to form a working cavity within tissue planes along the superior and inferior epigastric arteries. Side branches along the internal mammary, and superior epigastric and inferior gastric arteries thus isolated within the working cavity formed therealong may be occluded using surgical clips or sutures and ligated as required to isolate a length of the internal mammary artery and superior epigastric artery to provide a free distal end for anastomosis to the left descending coronary artery below a stenotic occlusion.

Figure 3:
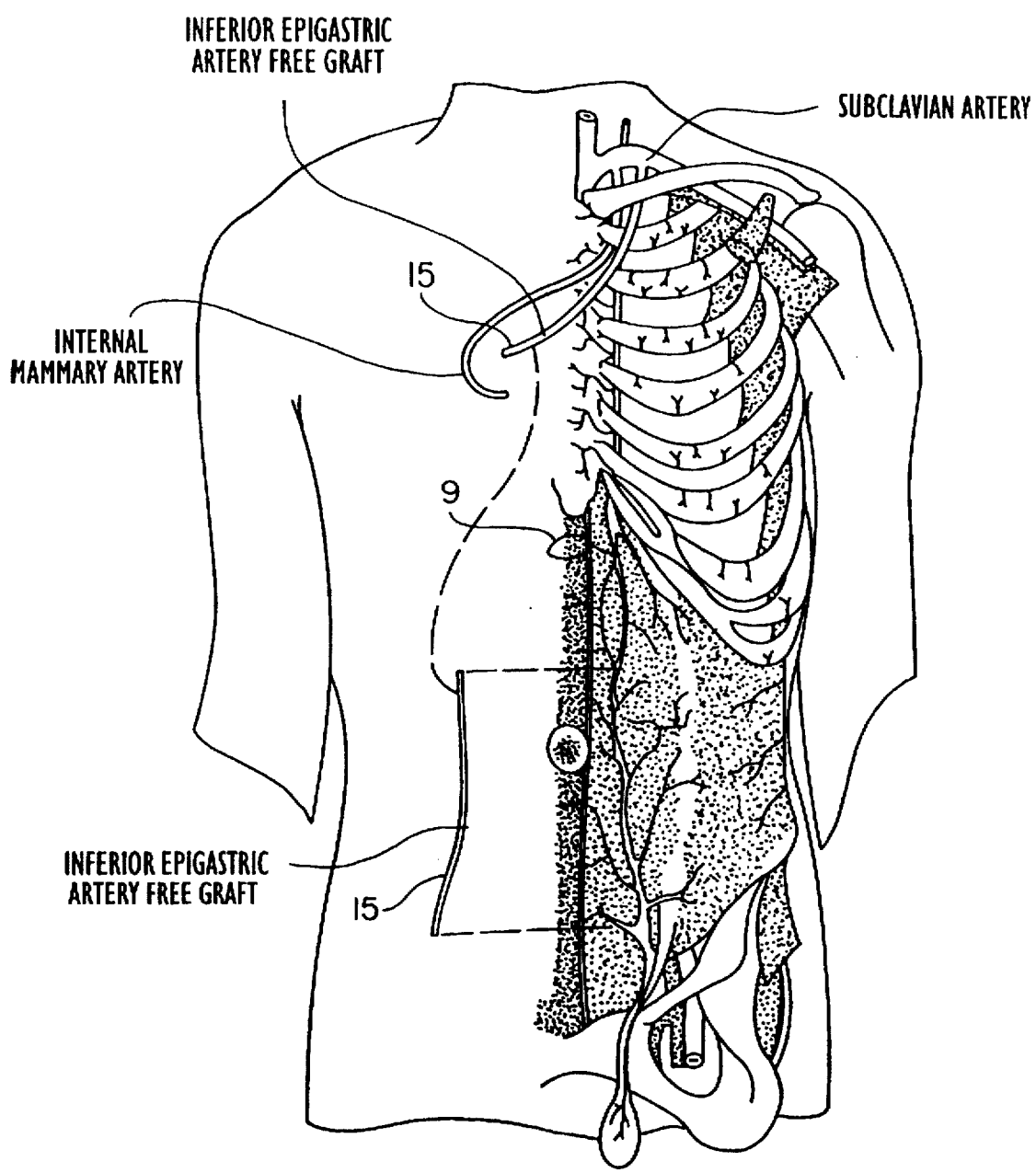
FIG. 3 is a partial anatomical drawing illustrating the inferior epigastric artery for free grafting to the subclavian artery.

As illustrated in the partial anatomical drawing of FIG. 3, a portion of the inferior epigastric artery below a distal free end of the artery may be harvested for additional bypass grafting between the subclavian artery and the coronary artery, as later described herein, all as accessed via the subcostal incision 9.

The procedures described above involve isolation of the superior epigastric artery, passage of the cannula 11 along the artery proximally to form a working cavity around the internal mammary artery, and passage of the cannula 11 distally to form a working cavity around the superior epigastric and inferior epigastric arteries.

Passage of the cannula 11 along the course of an artery is technically more difficult than passage of the same device along the course of a vein, due to the higher blood pressure present in arteries. Avulsion of even a small arterial side branch during advancement of the cannula results in bleeding which may be sufficient to obscure further cannula advancement.

The epigastric artery and vein, and the internal mammary artery and vein lie adjacent to each other. In an alternative procedure, both the superior epigastric artery and the superior epigastric vein may be isolated via a subxiphoid incision 9. The tapered tip balloon cannula 11 may be placed in contact with the superior epigastric vein, advanced superiorly along the internal mammary vein and inferiorly along the superior and inferior epigastric veins. The resultant working cavity formed around the epigastric and internal mammary veins also contains the adjacent arteries as well. However, since cannula passage occurs along the vein, any avulsion that occurs results in little or no bleeding, since the venous pressure is low. In some cases, avulsion of a small venous tributary causes no bleeding, since the interrupted ends of the venous tributaries go into spasm, and blood outflow is prevented. This situation is less likely to occur in arteries, since arterial side branches are under higher pressure.

Figure 6:
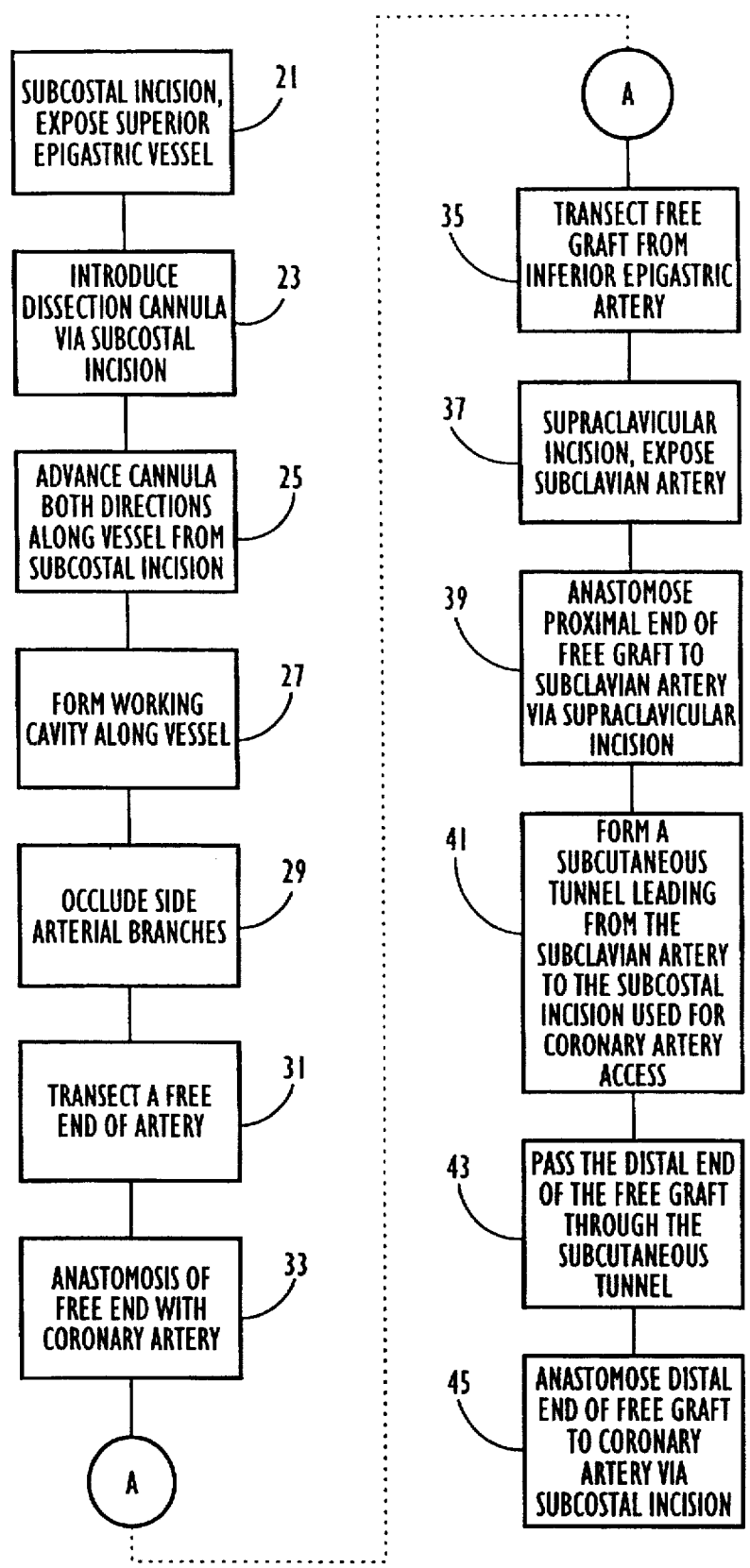
FIG. 6 is a flow chart illustrating the procedures of the present invention.

Referring now to the flow chart of FIG. 6, there is illustrated the procedure of the present invention for harvesting arterial vessels and for performing coronary bypasses via subcostal incision, and optionally for additional bypass conduits, via a supraclavicular incision.

Specifically, the subcostal incision is made 21 to expose the superior epigastric artery, a continuation of the internal mammary artery. The dissection cannula is then introduced 23 and advanced 25 along the internal mammary artery and the epigastric artery, in the superior and inferior directions relative to the subcostal incision for forming 27 a working cavity along the length of the internal mammary, superior epigastric and inferior epigastric arteries, substantially from the subclavian artery to the inferior epigastric arterial segment. Within the working cavity via the subcostal incision, the side arterial branches may be occluded 29 by surgical clips or sutures and ligated to prepare the internal mammary artery and its epigastric arterial continuation for transection 31 of a free end that may then be anastomosed 33 to a coronary artery via the subcostal incision.

Additionally, in patients requiring additional coronary bypass conduits, a free graft may be transected 35 from the inferior epigastric artery. A supraclavicular incision is formed 37 to expose the subclavian artery, and a proximal end of the free graft is anastomosed 39 to the subclavian artery via the supraclavicular incision. The free graft may then be routed above or beneath the clavicle and through a subcutaneous tunnel formed adjacent the sternum, and anastomosed 41 to a coronary artery via the subcostal incision for an additional coronary bypass conduit.

Therefore, successive cannula advances and inflation and deflation of the cannula balloon along the vein results in a working cavity within dissected tissue planes along the internal mammary vein and the superior and inferior epigastric veins. Such working cavity also provides convenient isolation of the adjacent artery, without introducing risk from arterial bleeding due to avulsion or other disruption of arterial side branches. Once the cavity is formed about the vein and artery, the artery may be skeletonized using a dissection probe and associated procedures as described in the Related Application, entitled "Tissue Dissection Cannula with Dissection Probe and Method", cited above.

Figure 4:
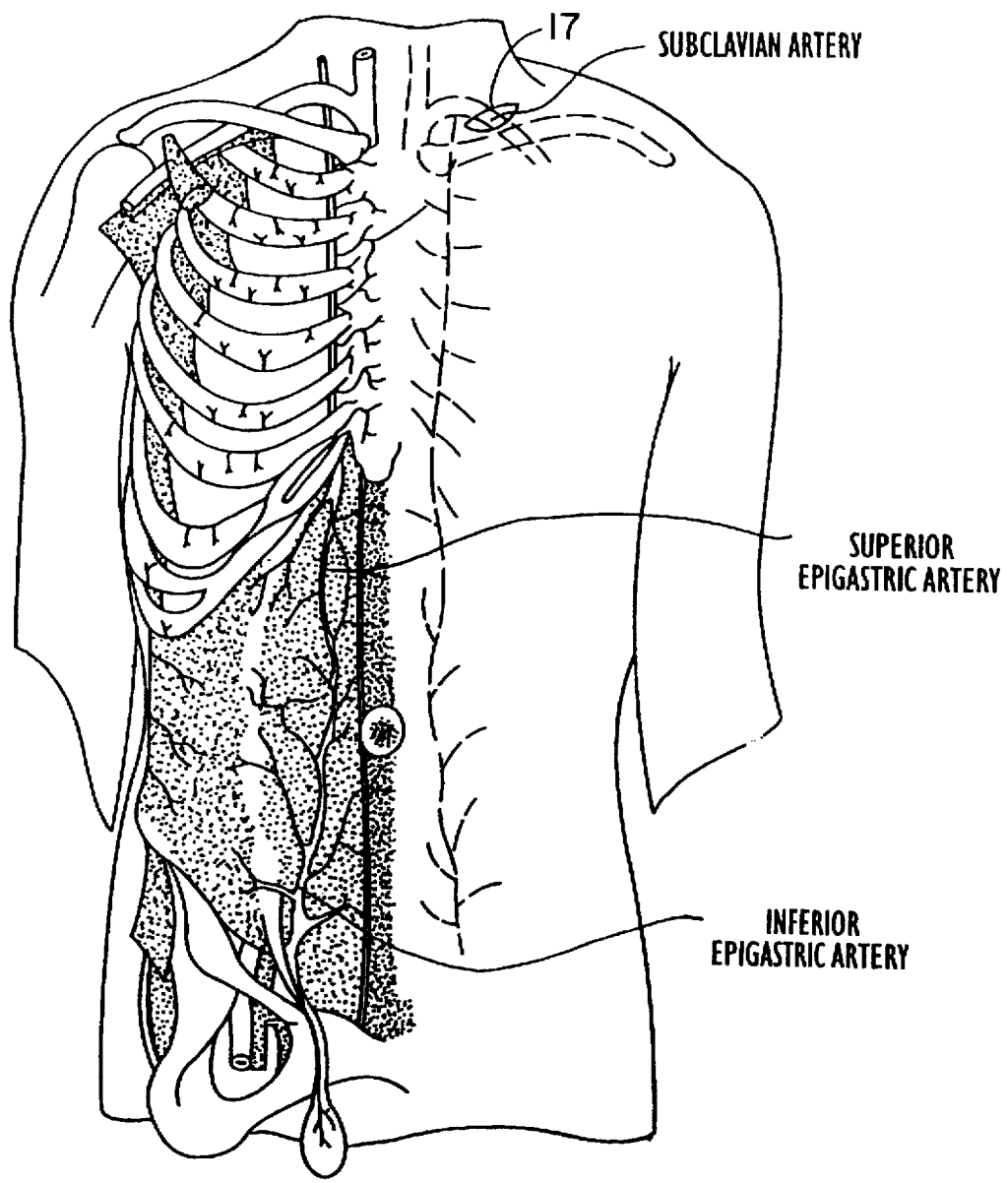
FIG. 4 is a partial anatomical drawing illustrating supraclavicular incision to expose the subclavian artery for grafting.
Figure 5:
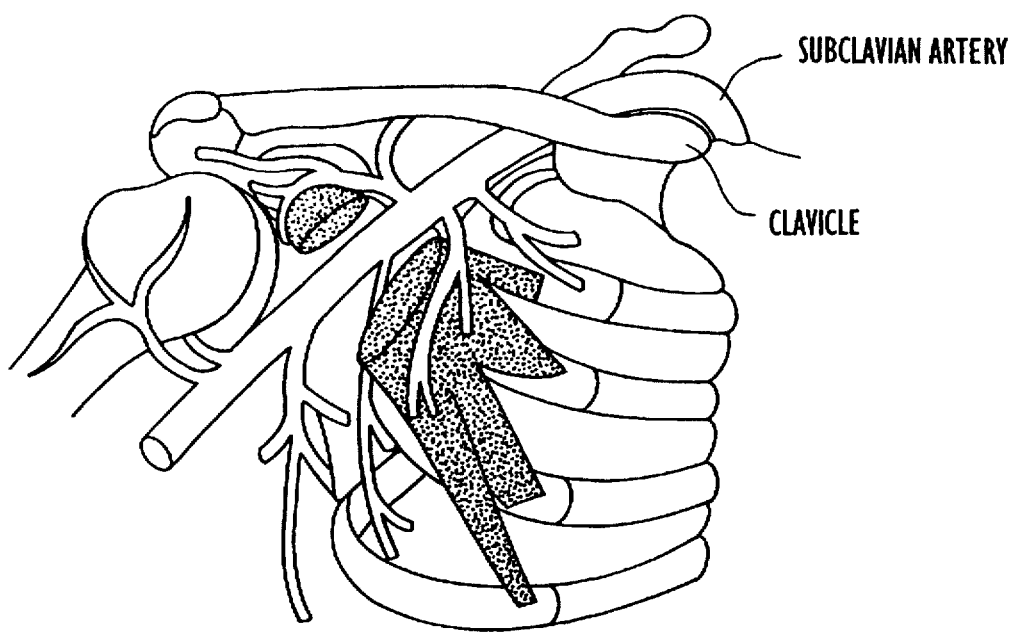
FIG. 5 is a partial anatomical drawing illustrating the region of the clavicle and subclavian and axillary arteries.

Referring now to the partial anatomical drawing of FIG. 4, there is shown a supraclavicular incision 17 that is oriented to expose the subclavian artery. The free graft of inferior epigastric artery, harvested in the manner previously described, may be anastomosed to the subclavian artery at this site to provide a second coronary bypass conduit, if necessary. The grafted inferior epigastric artery may pass anterior or posterior to the clavicle and through a subcutaneous tunnel formed adjacent the sternum, as illustrated in FIG. 5, to anastomosis with the left anterior descending coronary artery or other artery, such as diagonal branch of the left anterior descending artery, the circumflex artery, or an obtuse marginal branch from the circumflex artery, for additional arterial conduits around stenotic occlusions.

The segment of the coronary artery planned for a bypass anastomosis is dissected and isolated, and the artery is occluded proximal to the anastomosis site. An arteriotomy is performed at the anastomosis site by incising the artery with a scalpel and by extending the incision with Potts scissors. The distal end of the internal mammary artery graft or inferior epigaseric artery graft is positioned on the arteriotomy of the coronary artery, and the anastomosis is performed.

Therefore, the procedures according to the present invention facilitate isolation of the internal mammary artery and superior epigastric artery and inferior epigastric artery using minimal invasion through a subcostal incision and a tapered tip balloon dissection cannula for effective coronary bypass grafting via multiple arterial conduits.

I claim:

1. A method of harvesting an arterial vessel of a patient using a dissection cannula having a substantially rigid and transparent tissue-separating blunt tip covering a distal end of the cannula, and having a balloon attached to an exterior wall of the cannula near the blunt tip for peripheral expansion in response to selective inflation thereof, and having an endoscope disposed within the cannula with a viewing end positioned in alignment with the transparent tip for viewing therethrough tissue bluntly dissected thereby, the method comprising the steps of:

forming a subcostal incision to expose a superior epigastric vessel;

introducing the dissection cannula into the incision and advancing the blunt tip through tissue planes with visualization thereof through the blunt tip and endoscope while selectively inflating and deflating the balloon for sclectively dissecting the tissue planes to form a working cavity adjacent to and along the length of the arterial vessel substantially along the internal mammary artery to the region of the subclavian artery; and selectively occluding side branches from the internal mammary artery and providing a distal free end of the artery for anastomosis with a coronary artery.

2. The method according to claim 1 including the step of:

harvesting the inferior epigastric artery as a free graft for proximal anastomosis with the subclavian artery and distal anastomosis with a coronary artery as an additional coronary bypass conduit.

3. The method according to claim 1 wherein the step of introducing the dissection cannula includes selectively advancing the cannula along the course of the internal mammary vein to form a working cavity in dissected tissue planes adjacent the internal mammary artery.

4. The method according to claim 1 wherein the step of introducing the dissection cannula includes selectively advancing the cannula along the course of the vessel from the subcostal incision in the direction toward the subclavian artery.

5. The method according to claim 1 wherein the step of introducing the dissection cannula further includes selectively advancing the cannula along the course of the vessel from the subcostal incision in the direction remote from the subclavian artery to form a working cavity in dissected tissue planes along the course of the epigastric artery.

6. The method according to claim 1 in which the dissection cannula includes a transparent dissection tip for endoscopic visualization from within and through the tip, and where in the step of introducing, the tip and dissection cannula are advanced within tissue planes along the length of the arterial vessel under endoscopic visualization through the transparent tip substantially in contact with the arterial vessel.

7. A method for harvesting an arterial vessel of a patient using a dissection cannula comprising the steps of:

forming a subcostal incision to expose a superior epigastric vessel;

introducing the dissection cannula into the incision for selectively dissecting tissue planes to form a working cavity along the length of the arterial vessel substantially along the internal mammary artery to the region of the subclavian artery;

selectively occluding side branches from the internal mammary artery and providing a distal free end of the artery for anastomosis with a coronary artery;

harvesting the inferior epigastric artery as a free graft for proximal anastomosis with the subclavian artery and distal anastomosis with a coronary artery as an additional coronary bypass conduit;

forming a supraclavicular incision to expose the subclavian artery;

grafting an end of the harvested inferior epigastric artery to the subclavian artery substantially at the site of the supraclavicular incision; and grafting another end of the harvested inferior epigastric artery to a coronary artery.

8. A method for performing coronary artery bypass grafting using a balloon dissection cannula having a substantially rigid and transparent tissue-separating blunt tip covering a distal end of the cannula, and having a balloon attached to an exterior wall of the cannula near the blunt tip for peripheral expansion in response to selective inflation thereof, and having an endoscope disposed within the cannula with a viewing end positioned in alignment with the transparent tip for viewing therethrough tissue bluntly dissected thereby, the method comprising the steps of:

forming a subcostal incision to expose a superior epigastric vessel;

introducing the dissection cannula into the incision and selectively advancing the cannula through tissue planes with visualization thereof through the blunt tip and endoscope while selectively inflating and deflating the balloon to advance the cannula along the vessel in a superior direction toward the subclavian artery to form a working cavity along the vessel with intermittent advancement of the cannula and inflation of the balloon on the cannula;

introducing the dissection cannula into the incision and selectively advancing the cannula through tissue planes with visualization thereof through the blunt tip and endoscope while selectively inflating and deflating the balloon to advance the cannula along the vessel in an inferior direction away from the subclavian artery to form a working cavity along the vessel with intermittent advancement of the cannula and inflation of the balloon on the cannula;

selectively occluding side branches along the vessel, within the working cavity;

transecting the side branches within the working cavity; and transecting the distal end of the exposed vessel within the working cavity to provide an extended length of graft vessel.

9. The method according to claim 8 in which the balloon dissection cannula includes a transparent dissection tip for endoscopic visualization from within and through the tip, and wherein in each of the steps of introducing, the tip and dissection cannula are advanced within tissue planes along the length of the vessel in the advancing direction under endoscopic visualization through the transparent tip substantially in contact with the vessel.

10. A method for performing coronary artery bypass grafting using a balloon dissection cannula comprising the steps of:

forming a subcostal incision to expose a superior epigastric vessel;

introducing the dissection cannula into the incision and selectively advancing the cannula along the vessel in a superior direction toward the subclavian artery to form a working cavity along the vessel with intermittent advancement of the cannula and inflation of the balloon on the cannula;

introducing the dissection cannula into the incision and selectively advancing the cannula along the vessel in an inferior direction away from the subclavian artery to form a working cavity along the vessel with intermittent advancement of the cannula and inflation of the balloon on the cannula;

selectively occluding side branches along the vessel within the working cavity;

transecting the side branches within the working cavity;

transecting the distal end of the exposed vessel within the working cavity to provide an extended length of graft vessel;

transecting the internal mammary portion of the vessel to use as coronary graft, with a distal anastomosis to the coronary artery;

transecting the inferior epigastric portion of the vessel to use as a free graft; and forming a proximal anastomosis of the free graft to the subclavian artery and a distal anastomosis of the free graft to the subclavian artery and a distal anastomosis of the free graft to the coronary artery.

11. A method for performing coronary artery bypass grafting using a balloon dissection cannula comprising the steps of:

forming a subcostal incision to expose a superior epigastric vessel;

introducing the dissection cannula into the incision and selectively advancing the cannula along the vessel in a superior direction toward the subclavian artery to form a working cavity along the vessel with intermittent advancement of the cannula and inflation of the balloon on the cannula;

introducing the dissection cannula into the incision and selectively advancing the cannula along the vessel in an inferior direction away from the subclavian artery to form a working cavity along the vessel with intermittent advancement of the cannula and inflation of the balloon on the cannula;

selectively occluding side branches along the vessel, within the working cavity;

transecting the side branches within the working cavity;

transecting the distal end of the exposed vessel within the working cavity to provide an extended length of graft vessel; and anastomosing the free end of the internal mammary artery to the coronary artery and the free end of the inferior epigastric portion of the graft vessel to the coronary artery, while the heart is in a beating state.

12. A method for performing coronary artery bypass grafting using a balloon dissection cannula comprising the steps of:

forming a subcostal incision to expose a superior epigastric vessel;

introducing the dissection cannula into the incision and selectively advancing the cannula along the vessel in a superior direction toward the subclavian artery to form a working cavity along the vessel with intermittent advancement of the cannula and inflation of the balloon on the cannula;

introducing the dissection cannula into the incision and selectively advancing the cannula along the vessel in an inferior direction away from the subclavian artery to form a working cavity along the vessel with intermittent advancement of the cannula and inflation of the balloon on the cannula;

selectively occluding side branches along the vessel, within the working cavity;

transecting the side branches within the working cavity;

transecting the distal end of the exposed vessel within the working cavity to provide an extended length of graft vessel;

forming a tunnel from the subclavian artery at the supraclavicular incision to the parasternal subcostal incision used for access to the heart and coronary artery; and positioning the free end of the inferior epigastric portion of the graft vessel though the tunnel for anastomosis to the coronary artery.

13. The method according to claim 12, including the steps of:

repeating the steps for harvesting one or more of the internal mammary artery and inferior epigastric artery on the opposite sides of the patient to yield up to four coronary artery bypass grafts.

14. The method according to claim 13 in which the steps are performed on a beating heart.

* * * * *